United States Patent [19]
Broekhof

[11] Patent Number: 4,689,175
[45] Date of Patent: Aug. 25, 1987

[54] PERFUME COMPOSITIONS AND PERFUMED ARTICLES AND MATERIALS WHICH CONTAIN DERIVATIVES OF M-CRESOL AS PERFUME COMPONENT

[75] Inventor: Nicolaas L. J. M. Broekhof, Naarden, Netherlands

[73] Assignee: Naarden International N.V., Ussum, Netherlands

[21] Appl. No.: 896,399

[22] Filed: Aug. 13, 1986

[30] Foreign Application Priority Data

Aug. 21, 1985 [NL] Netherlands ........................ 8502304

[51] Int. Cl.[4] ......................... A61K 7/446; C11B 9/00

[52] U.S. Cl. ...................................... 512/20; 568/780; 568/781

[58] Field of Search .................... 252/522 R; 568/780, 568/781

[56] References Cited

PUBLICATIONS

Gura et al., "Chemical Abstracts", vol. 61, p. 15927e.

Gura et al., "Chemical Abstracts", vol. 64, pp. 4960–4961x.

*Primary Examiner*—Werren B. Lone
*Attorney, Agent, or Firm*—Brumbaugh, Graves, Donohue & Raymond

[57] ABSTRACT

Perfume compositions and perfumed products characterized by a content of one or more fragrances which have a very natural leather odor and correspond to the formula

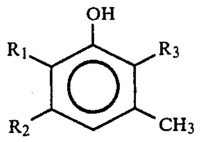

(I)

wherein one of the two symbols $R_1$ and $R_2$ represents a methyl group and the other a hydrogen atom or both symbols represent a hydrogen atom and $R_3$ represents a n-propyl, allyl, 1-propenyl-, sec.butyl, 1-buten-3-yl, isobutyl or 2-methylpropen-3-yl group.

7 Claims, No Drawings

PERFUME COMPOSITIONS AND PERFUMED ARTICLES AND MATERIALS WHICH CONTAIN DERIVATIVES OF M-CRESOL AS PERFUME COMPONENT

The invention relates to perfume compositions which contain derivatives of m-cresol as perfume component and to articles and materials perfumed with such derivatives or compositions containing such derivatives respectively.

There is a lasting interest in the preparation and use of synthetic perfumes because, in contrast to natural products, they can always be prepared in a quantity which is matched to the demand and with a constant quality.

Leather has a characteristic, very complex but also very valued odour. Until now a leather odour could only be approximated to by combinations of many components known per se in the perfume industry. Important components of such leather-odour compositions are birchtar oil and some substituted phenols and phenol ethers, in particular p-tert-butylphenol, p-tert-butyl-m-cresol and their methyl ethers. These compounds are characterized by a phenolic phenolic and somewhat medicinal odoriferous character. Although a phenolic note is an important aspect of the odour in the overall odour of leather, said compounds nevertheless have too little leather character to result in a really satisfactory leather odour.

It has now been found that ortho-alkyl- or alkenyl-substituted m-cresols having the formula:

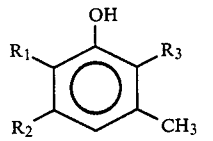

(I)

wherein one of the two groups $R_1$ and $R_2$ represents a methyl group and the other hydrogen, or both represent hydrogen and wherein $R_3$ represents one of the groups n-propyl, , allyl, 1-propenyl, sec-butyl, 1-buten-3-yl, isobutyl, 2-methylpropene-3-yl, are powerful and stable fragrances with a very natural leather odour.

Various substituted phenols are known in the perfume industry, some of which have a leather-type note. Mention has already been made of p-tert-butylphenol (S. Arctander, Perfumes and Flavor Chemicals, monograph No. 504) and p-tert-butyl-m-cresol (Arctander No. 429). Arctander also mentions further p-tert-amly-phenol (No. 205), 2-tert-butyl-4,5-dimethylphenol (No. 446), 4-tert-butyl-3,5-dimethylphenol (No. 546), chavicol (No. 606), m-cresol (No. 707) and o-ethylphenol (No. 1328). Insofar as the compounds mentioned above contain an alkyl group of 3 or more C atoms, they are characterized by a 4-alk(en)ylphenol structure, with the sole exception of (no. 446) but according to Arctander this finds little or no use as a fragrance.

On the other hand, the compounds according to the invention are characterized by a 2-alk(en)yl-3-methyl-phenol-substituted pattern which is not found in any of the known compounds. In addition, the known compounds do indeed exhibit a somewhat phenolic leather-type note, but none of them has a complete and natural leather odour like the compounds according to the invention.

The other substituted phenols known in the perfume industry such as carvacrol (Arctander No. 573), 2,4-dimethyl-6-isopropylphenol (No. 1054), thymol (No. 2944), isothymol (No. 2945) and xylenol (No 3098), do not even exhibit any leather character at all. Said compounds mostly have medicinal and spicy odours. Thymol is, in addition, used in mandarin aroma (see Dutch patent application No. 6,403,357).

The compounds according to the invention are very suitable for use as such, or in combination with other components usual for the purpose, to impart a fine and natural leather odour to all kinds of articles and materials. The compounds may also be used with advantage in perfume compositions in which a leather note is desirable. In particular, the compounds 2-allyl-3-methyl-phenol, 2-allyl-3,6-dimethylphenol, 2-(prop-1-enyl)-3-methylphenol, 2-sec-butyl-3-methylphenol and 2-isobutyl-3-methylphenol excel in their fine and very long-lasting leather odour.

Here the term "perfume composition" means a mixture of fragrances and optional auxilliary substances, if required dissolved in a suitable solvent or mixed with a powdered substrate, which is used to impart a desired odour to the skin and/or all kinds of products. Examples of such products are: soaps, detergents, air fresheners, room sprays, pomanders, candles, cosmetics, such as creams, ointments, toilet waters, pre and aftershave lotions, talcum powders, hair-care products, body deodorants and antiperspirants. The compounds according to the invention are also very suitable per se for imparting a leather odour to all types of products such as leather-substitute materials.

Fragrances and mixtures of perfumes which may be used in combination with the compounds according to the invention for the preparation of perfume compositions are, for example: natural products usch as ethereal oils, absolute oils, resinoids, resins, concrete oils etc, but also synthetic fragrances such as hydrocarbons, alcohols, aldehydes, ketones, ethers, acids, esters, acetales, ketales, nitriles, etc, including saturated and unsaturated compounds, aliphatic, carbocyclic and heterocyclic compounds. Examples of fragrances which may be used in combination with the compounds according to the invention are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)propanal, 3-(p-tert-butylphenyl)propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy3-pentyl-tetrahydropyran, 3-carboxymethyl-2-pentyl-cyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethylacetale, phenylacetaldehyde diethylacetale, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan-musks, tetralin-musks, isochroman-musks, macrocyclic ketones, macrolactone-musks, ethylene brassylate, aromatic nitro-musks.

Auxilliary materials and solvents which may be used in perfume compositions which contain compounds according to the invention are for example: ethanol, isopropanol, diethyleneglycol monoethyl ether, diethyl phthalate etc.

The quantities in which the compounds according to the invention may be used in perfume compositions or products to be perfumed may vary within wide limits, and depend, inter alia, on the nature of the product in which the perfume is used , on the nature and the quantity of the remaining components in the perfume composition and on the odour effect which is aimed at. Consequently, it is possible to specify only very rough limits which, however, provide those skilled in the art with sufficient information to be able to use the compounds according to the invention independently. In most cases a quantity of only 0.1% by weight in a perfume composition will already be sufficient to obtain a clearly perceptible odour effect. On the other hand, to achieve special odour effects, it is possible to use quantities of 90% by weight or even more in a composition. In product perfumed by means of perfume compositions these concentrations are proportionately lower depending on the quantity of composition used in the product.

The compounds according to the invention may be prepared by methods described in the literature for these and similar compounds, in particular by Claisen rearrangement of suitable phenyl alkenyl ethers which may be prepared in their turn by standard methods from m-cresol, or 3,5- or 3,6-dimethylphenol and allyl-, or butenyl or isobutenylhalide. Both the preparation of the phenyl alkenyl ethers and the Claisen rearrangement subsequent thereto are extensively described in Organic Reaction, Volume II, John Wiley & Sons, Inc., New York 1944, pages 1–48. The compounds wherein $R_3$ is propyl, isobutyl or sec-butyl, are obtained from the corresponding unsaturated compounds by catalytic hydrogenation by standard methods, e.g. by means of 5% Pd on carbon at atmospheric or increased pressure. The compounds wherein $R_3$ represents 1-propenyl can be obtained by alkaline isomerization of the corresponding allyl compounds, e.g. by means of 1.1 equivalent of potassium tert-butylate in dimethyl sulphoxide, for 2 hours at 70° C., or as described in Organic Reactions Volume II, page 27.

If $R_1=R^2=H$, in the synthesis a 1:1 mixture is obtained of the desired compound according to the invention and the corresponding 6-alk(en)yl-3-methylphenol. These latter isomers have a phenolic odour with little leather character and are therefore not part of the invention. As already mentioned above, in many types of leather a phenolic note is an important aspect of the odour in the overall leather odour The presence of said isomers does not therefore have any disadvantageous effect on the applicability of the compounds according to the invention as leather fragrances in perfume compositions or materials to be perfumed. The isomer mixtures obtained in the synthesis may therefore be used as leather fragrances without further separation. However, it is also quite possible to separate the two isomers by means of chromatographic techniques, e.g. HPLC over silica gel modified with cyan groups so that, if required, the pure 2-alk(en)yl-3-methylphenol may nevertheless be used.

The following examples serve purely to illustrate the application of the compounds according to the invention. The invention is, however, not limited thereto.

EXAMPLE I

Preparation of 2-allyl-3-methylphenol 360 g of a 30% solution of sodium methylate in methanol were added to a mixture of 139 g of allyl chloride and 216 g of m-cresol in 15 minutes, the temperature being kept below 40° C. by cooling. Stirring was then carried out at approx. 45° C. or a further 4 hours, after which the reaction was terminated by pouring out the reaction-mixture into a mixture of 150 g of concentrated hydrochloric acid and 700 g of ice. 200 g of toluene were then added, stirred thoroughly and the layers were separated. The organic layer was washed neutrally with saturated sodium bicarbonate solution. After adding 4 g of solid soda, approx. 160 g of toluene were evaporated off. The remaining mixture was heated at 200° C. while stirring for 4 hours, all the volatile components being distilled off. The Claisen rearrangement was terminated by allowing the mixture to cool. Fractionation was then carried out at reduced pressure.

156 g of a mixture of 2-allyl- and 6-allyl-3-methylphenol, b.p. 98° C./1.1 kPa, were obtained. The mixture had a fine leather odour with a correct dose of phenolic note.

Pure 2-allyl-3-methylphenol was obtained by separating the mixture by means of HPLC via a Zorbax CN* column using a mixture of 99% pentane and 1% isopropanol as eluent. This compound had a fine odour with the typical character of fresh leather.

*Marketed by E. I. Dupont de Nemours.

EXAMPLE II

A perfume composition for a "man's cologne" was prepared according to the following recipe:

| | |
|---|---|
| acetylcedrene | 140 parts by weight |
| bergamot oil | 130 parts by weight |
| lemon oil | 65 parts by weight |
| α-hexylcinnamaldehyde | 65 parts by weight |
| lavandin oil | 50 parts by weight |
| methyl dihydrojasmonate | 40 parts by weight |
| patchouli oil | 40 parts by weight |
| 5-acetyl-3-isopropyl-1,1,2,6-tetramethylindan | 30 parts by weight |
| lily of the valley, synthetic | 30 parts by weight |
| isolongifolanone | 30 parts by weight |
| aspic oil | 30 parts by weight |
| musk ketone | 20 parts by weight |
| labdanum resinoid | 20 parts by weight |
| ylang-ylang oil | 20 parts by weight |
| menthol | 10 parts by weight |
| mousse de chene absolute | 10 parts by weight |
| isobutylquinoline* | 10 parts by weight |
| galbanum oil* | 10 parts by weight |
| undecylene aldehyde* | 5 parts by weight |
| methylnonylacetaldehyde* | 5 parts by weight |
| styrallyl acetate | 5 parts by weight |
| clove oil | 5 parts by weight |
| product obtained according to Example I | 30 parts by weight |
| | 800 parts by weight |

*10% solution by weight in diethyleneglycol monoethyl ether.

EXAMPLE III

A perfume composition for an aftershave lotion was prepared according to the recipe below:

| | |
|---|---|
| cedryl acetate | 230 parts by weight |
| patchouli oil | 100 parts by weight |
| lemon oil | 100 parts by weight |
| lavender oil | 100 parts by weight |
| benzyl salicylate | 90 parts by weight |
| musk ketone | 53 parts by weight |
| bergamot oil | 50 parts by weight |
| rose, synthetic | 50 parts by weight |
| coumarin | 30 parts by weight |
| jasmin, synthetic | 30 parts by weight |
| methyl dihydrojasmonate | 30 parts by weight |
| amber, synthetic | 25 parts by weight |
| galbanum resinoid | 20 parts by weight |
| sandlewood oil, East Indian | 20 parts by weight |
| geranium oil, Bourbon | 20 parts by weight |
| mousse de chene absolute | 10 parts by weight |
| basil oil | 10 parts by weight |
| origanum oil | 2 parts by weight |
| 2-allyl-3,6-dimethylphenol | 30 parts by weight |
| | 1,000 parts by weight |

EXAMPLE IV

An aftershave lotion perfumed with the composition according to Example III was prepared according to the recipe below:

A. 0.3 parts by weight of l-menthol; 0.5 parts by weight of uvinol D 50(*); 30.0 parts by weight of propyleneglycol; 535 parts by weight of ethanol.

B. 2.0 parts by weight of aluminium chlorohydrate allantoate; 2.0 parts by weight of lactic acid; 400 parts by weight of water (distilled).

C. 20 parts by weight of perfume (Example III); 10 parts by weight of cremophor RH40(**).

The components mentioned under A., B. and C. were mixed separately to form the mixtures A., B. and C. The mixture B was then added to mixture A while stirring thoroughly. Mixture C was then added and the total mixture was homogenised by stirring. In this way, a somewhat astringent aftershave lotion was obtained, the odour of which was characterized by a pleasant leather note.

(*)BASF trade mark for 2,2',4,4'-tetrahydroxybenzofuran (**)BASF trade mark for a reaction product of hydrogenated resinous oil epoxyethane.

I claim:

1. A perfume composition comprising an effective odorant amount of one or more fragrancing compounds of the formula

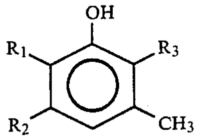

(I)

wherein one of the symbols $R_1$ and $R_2$ represents a methyl group and the other is a hydrogen atom or both symbols represent a hydrogen atom, and $R_3$ represents an n-propyl, allyl, 1-propenyl, sec-butyl, 1-buten-3-yl, isobutyl or 2-methylpropenyl group, together with customary perfumery ingredients.

2. A perfume composition according to claim 1, comprising an effective odorant amount of one or more compounds selected from the group consisting of 2-allyl-3-methylphenol, 2-allyl-3,6-dimethylphenol, 2-(prop-1-enyl)-3-methylphenol, 2-sec-buty-3-methylphenol and 2-isobutyl-3-methylphenol.

3. A perfume composition according to claim 1, comprising at least 0.1% by weight of the fragrancing compounds given by formula (I).

4. A perfumed product comprising an effective odorant amount of one or more fragrancing compounds of the formula

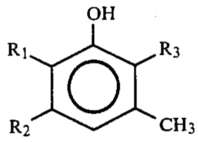

(I)

wherein one of the symbols $R_1$ and $R_2$ represents a methyl group and the other is a hydrogen atom or both symbols represent a hydrogen atom, and $R_3$ represents an n-propyl, allyl, 1-propenyl, sec-butyl, 1-buten-3-yl, isobutyl or 2-methylpropenyl group.

5. A perfumed product according to claim 4, comprising an effective odorant amount of one or more compounds selected from the group consisting of 2-allyl-3-methylphenol, 2-allyl-3,6-dimethylphenol, 2-(prop-1-enyl)-3-methylphenol, 2-sec-butyl-3-methylphenol and 2-isobutyl-3-methylphenol.

6. A method of imparting a leathery note to a material comprising adding to said material an effective odorant amount of one or more compounds of the formula

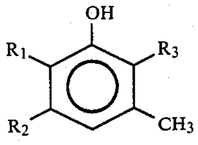

(I)

wherein one of the symbols $R_1$ and $R_2$ represents a methyl group and the other is hydrogen atom or both symbols represent a hydrogen atom, and $R_3$ represents an n-propyl, allyl, 1-propenyl, sec-butyl, 1-buten-3-yl, isobutyl or 2-methylpropenyl group.

7. A method according to claim 6, wherein the compound added is selected from the group consisting of 2-allyl-3-methylphenol, 2-allyl-3,6-dimethylphenol, 2-(prop-1-enyl)-3-methylphenol, 2-sec-butyl-3-methylphenol and 2-isobutyl-3-methylphenol.

* * * * *

UNITED STATES PATENT AND TRADEMARK OFFICE
CERTIFICATE OF CORRECTION

PATENT NO. : 4,689,175

DATED : August 25, 1987

INVENTOR(S) : Nicolaas L. J. M. Broekhof

It is certified that error appears in the above-identified patent and that said Letters Patent is hereby corrected as shown below:

First Page, Item 73, "Ussum" should read --Naarden-Bussum--.

The references listed in our Form PTO-1449 filed November 10, 1986 have not been included on the first page of the patent. The "Notice of Allowability" shows said form as an "Attachment", but it is not attached thereto. The references to be listed are:

| | |
|---|---|
| --78353 | France |
| 6403357 | Netherlands |

S. ARCTANDER: "Perfume and Flavor Chemicals," 1969, Aroma Chemicals I., Montclair, N.J. Nos. 205, 429, 446, 504, 546, 573, 606, 707, 1054, 1328, 2944, 2945, 3098.--

Col. 1, line 50, "amly-" should read --amyl- --;

UNITED STATES PATENT AND TRADEMARK OFFICE

CERTIFICATE OF CORRECTION

PATENT NO. : 4,689,175

DATED : August 25, 1987

INVENTOR(S) : Nicolaas L. J. M. Broekhof

It is certified that error appears in the above-identified patent and that said Letters Patent is hereby corrected as shown below:

Col. 2, line 58, "4-acetoxy3" should read --4-acetoxy-3 --;

Col. 3, line 38, "Reaction" should read --Reactions--;

Col. 5, line 43, after "oil" insert --and--; and

Col. 6, line 48, after "is" insert --a--.

Signed and Sealed this

Nineteenth Day of April, 1988

Attest:

DONALD J. QUIGG

Attesting Officer

Commissioner of Patents and Trademarks